US00PP08476P

United States Patent [19]

Suzuki

[11] Patent Number: Plant 8,476

[45] Date of Patent: Nov. 30, 1993

[54] ROSE PLANT KEIBIAN

[75] Inventor: Seizo Suzuki, Yachiyo, Japan

[73] Assignee: Bear Creek Gardens, Inc., Medford, Oreg.

[21] Appl. No.: 971,506

[22] Filed: Nov. 4, 1992

[51] Int. Cl.[5] ..... A01H 5/00

[52] U.S. Cl. ..... Plt./11

[58] Field of Search ..... Plt. 11, 12

*Primary Examiner*—Howard J. Locker

*Assistant Examiner*—E. F. McElwain

*Attorney, Agent, or Firm*—Klarquist Sparkman Campbell Leigh & Whinston

[57] ABSTRACT

Hybrid tea rose plant having distinctive color change in sunlight as the flower ages; a heavy, sweet fragrance; a vigorous, upright growth habit; dark green, disease resistant foliage, and the presence of glands on stipules and peduncles.

1 Drawing Sheet

The present invention relates to a new and distinct variety of rose plant of the hybrid tea class which was originated by me by crossing an unnamed seedling with an unnamed seedling.

The primary objective of this breeding was to produce a new rose variety having a flower that changed from yellow to red like its female parent and also had a good fragrance like that of its male parent. The objective was substantially achieved along with other desirable improvements as evidenced by the following unique combination of characteristics which are outstanding in the new variety and which distinguish it from its parents, as well as from all other varieties of which I am aware:

1. An intense heavy, sweet fragrance;
2. An attractive intensification of flower color from a very light yellow to a pink to red on the petal margins;
3. Deep glossy green, disease resistant foliage;
4. Presence of many glands on peduncles and stipules;
5. Upright, vigorous habit of growth.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Rose hybrida.

*Commercial.*—Hybrid tea.

FLOWER

Observations made from specimens grown in a garden in Somis, Calif. from Mar. to Aug., 1992.

Blooming Habit: Recurrent.

Bud

*Size.*—1½ inches when the petals start to unfurl.

*Form.*—Long, pointed ovoid.

*Color.*—When sepals first divide, bud is a mixture of colors: Red Group 43B on those areas most exposed to the sun, changes to Red Group 43D on areas less exposed and on areas least exposed is Yellow Orange Group 18D. When half blown, the upper sides of the outer petals are Red Group 43B on the edes shading to Red Group 43C then 43D finally shading to Yellow Orange Group 18D; and the lower sides of the petals are Red Group 43B to D on areas exposed to the sun; otherwise Yellow Orange Group 18D.

*Sepals.*—Color: Green Group 138C with a reddish cast. Surface texture: Covered in fine hairs. There are three lightly appendaged sepals. There are two unappendaged sepals with hairy edges.

*Receptacle.*—Color: Green Group 138B. Shape: Apple. Size: Medium (6/16×5/16 inches). Surface: Smooth.

*Peduncle.*—Length: Medium (3½ to 4 inches). Surface: Glandular. Color: Medium green. Strength: Stiff, erect.

Bloom:

*Size.*—Large. Average open size is 5 inches.

*Borne.*—Singly.

*Stems.*—Medium (16 to 18 inches).

*Form.*—When first open: High centered. Permanence. Retains its form to the end; outer petals curl back.

*Petalage.*—Number of petals under normal conditions: 30.

*Color.*—The upper side of the petals is Red Group 43B on petal edges most exposed to sun changing to Red Group 43C to D on less exposed surfaces; least exposed are Yellow orange Group 18D. The reverse side of the petals is the same sequence but because so little of the petal underside is exposed to the sun, most of the color is Yellow Orange Group 18D. The bases of the petals have a small (¼×¼ inches) yellow half moon Yellow Orange Group 14A at the point of attachment. The major color on the upper side is Yellow Orange Group 18D.

*Variegations.*—None.

*Discoloration.*—The general tonality at the end of the first day: Little change. At the end of the third day, Gradual increase in color change from Yellow Orange Group 18D to more Red Group 43B through D.

*Fragrance.*—Strong.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Fair (4 to 5 days). As a cut flower: Fair (6 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: White.

*Stigmas.*—Color: Greenish white.

Form: Bush.

Growth: Very vigorous, upright, branching.

Foliage:

*Number of leaflets on normal mid-stem leaves.*— 5 or 7.

*Size.*—Large (6×5 inches).

*Quantity.*—Abundant.

*Color.*—New foliage: Reddish. Old foliage: Dark green, glossy.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth with occasional prickles.

*Stipules.*—Medium, bearded and edged with glands.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its color change in sunlight as the flower ages; a heavy, sweet fragrance; a vigorous, upright growth habit; dark green, disease resistant foliage, and the presence of glands on stipules and peduncles.

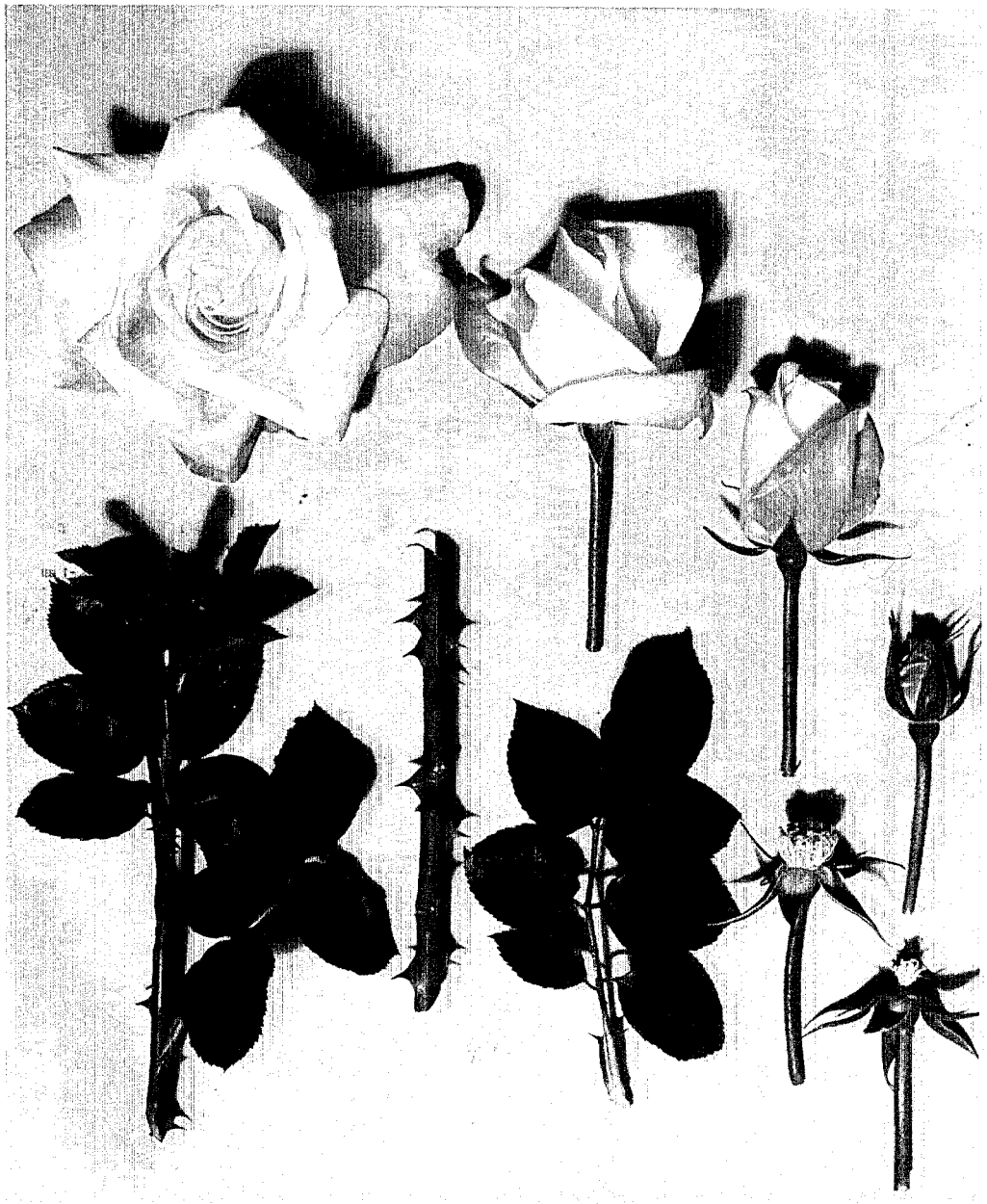

* * * * *